United States Patent
Kwon et al.

(10) Patent No.: US 11,800,871 B2
(45) Date of Patent: Oct. 31, 2023

(54) PAENIBACILLUS ELGII AM-67 STRAIN AND BIOPESTICIDE COMPOSITION CONTAINING SAME

(71) Applicant: ANDONG NATIONAL UNIVERSITY INDUSTRY—ACADEMIC COOPERATION FOUNDATION, Andong-si (KR)

(72) Inventors: Gi Seok Kwon, Andong-si (KR); Jung Bok Lee, Andong-si (KR); Dan Bi Lee, Gyeongsangbuk-do (KR)

(73) Assignee: Andong National University Industry-Academic Cooperation Foundation, Andong-si (KR)

( * ) Notice: Subject to any disclaimer, the term of this patent is extended or adjusted under 35 U.S.C. 154(b) by 236 days.

(21) Appl. No.: 16/789,942

(22) Filed: Feb. 13, 2020

(65) Prior Publication Data

US 2020/0187508 A1    Jun. 18, 2020

Related U.S. Application Data

(63) Continuation of application No. PCT/KR2018/001253, filed on Jan. 29, 2018.

(30) Foreign Application Priority Data

Jan. 22, 2018 (KR) .......... 10-2018-0007953
Jan. 29, 2018 (KR) .......... 10-2018-0010792

(51) Int. Cl.
*A01N 63/25* (2020.01)
*C12N 1/20* (2006.01)

(52) U.S. Cl.
CPC .............. *A01N 63/25* (2020.01); *C12N 1/20* (2013.01)

(58) Field of Classification Search
CPC ................................. A01N 63/25; C12N 1/20
See application file for complete search history.

(56) References Cited

U.S. PATENT DOCUMENTS

| 2008/0182790 A1 | 7/2008 | Zhang et al. |
| 2016/0278388 A1 | 9/2016 | Beau et al. |

FOREIGN PATENT DOCUMENTS

| KP | 10-0580336 B | 5/2006 |
| KR | 10-2003-0065468 A | 8/2003 |
| KR | 10-0743672 B | 7/2007 |
| KR | 10-1010537 B | 1/2011 |
| KR | 10-1206883 B | 12/2012 |
| KR | 10-2015-0101702 A | 9/2015 |
| KR | 10-2016-0041084 A | 4/2016 |
| KR | 10-2017-0129921 A | 11/2017 |

OTHER PUBLICATIONS

Chung et al., *The Korean Journal of Pesticide Science*, vol. 7, No. 1, pp. 32-37, 2003.
De Boer et al., "Influence of oxygen concentration end storage factors on susceptibility of potato tubers to bacterial soft rot (*Erwinia carotovora*)", *Potato Res.*, 21, 1978, pp. 65-80.
International Search Report dated Feb. 8, 2019 in International Application No. PCT/KR/2018/001253, in 2 pages.
Office Action dated Mar. 13, 2019 in Korean Application No. 10-2018-0010792, in 10 pages.
Kuo et al., "Associations between heat tolerance, water consumption, and morphological characters in Chinese cabbage", *Euphytica*, 39, pp. 85-73, 1988.
Kwon et al., "Isolation and Characterization of Plant Pathogen that Cause Soft Rot Disease in Napa Cabbage", *Journal of Life Science*, vol. 19, No. 8, pp. 1177-1182, 2809.
Lee, "Isolation and Cultural Condition of *Paenibacillus elgii* AM-67, and Characteristics of Antimicrobial Substance Against Chinese Cabbage (*Brassica rapa* subsp. *pekinensis*) Soft Rot", Thesis for the Degree of master of Science, Andong National University, Dec. 2016, in 78 pages.
Stommel et al., "Pepper (*Capsicum annum*) Soft Rot Caused by *Erwinia carotovora* subsp. *atroseptica*", *Plant Disease*, vol. 80, No. 10, Oct. 1996, pp. 1109-1112.
Wu et al., "Isolation and partial characterization of antibiotics produced by *Paenibacillus elgii* B69", *FEMS Microbiol Lett*, 310, pp. 32-38, 2019.
OPEÑA et al., "Breeding and Seed Production of Chinese cabbage in the Tropics and Subtropics", Technical Bulletin No. 17. Shanshua, Taiwan: Asian Vegetable Research and Development Center (AVRDC), May 1988, in 92 pages.
Shrestha et al., "Antagonistic Effect of Lactobacillus sp. Strain KLF01 Against Plant Pathogenic Bacteria Ralstonia solanacearum", The Korean Journal of Pesticide Science, vol. 13, No. 1, pp. 45-53, 2009.
Accession KCTC 13466BP (date of deposit: Jan. 23, 2018).
GenBank Accession No. 113885, Nov. 10, 2011 (last modified Feb. 3, 2015).

*Primary Examiner* — Robert A Zeman
(74) *Attorney, Agent, or Firm* — Knobbe Martens Olson & Bear LLP

(57) ABSTRACT

The present disclosure relates to a novel strain for inhibiting a Chinese cabbage soft rot disease from microorganisms isolated from samples of a *bacillus* source of soil polluted with a soft-rot disease, a culture medium and crude extract using the culture medium, an environmentally friendly plant disease control agent using same, and a method for utilizing same as an environment-friendly preparation biopesticide by using same as a raw material. The present disclosure also relates to a control method for treating soils or plants using an environmentally friendly Chinese cabbage soft-rot disease control agent through various formulation methods by using the strain, a culture medium thereof, and a crude extract thereof.

2 Claims, 3 Drawing Sheets
Specification includes a Sequence Listing.

Genetic map of strain AM-67

[Note] Circos map was drawn by applying contig 1's annotation result. Marked characteristics are shown from outside to the center: CDS on forward strand, CDS on reverse strand, tRNA, rRNA, GC content and GC skew.

[Note] A : *Erwinia carotovora*, B : *Erwinia carotovora* KACC10225, C : *Erwinia carotovora* KACC10342, D : *Erwinia carotovora* KACC10371, E : *Erwinia carotovora* KACC10458
a : $CHCl_3$ layer, b : $CHCl_3$ control

SEQUENCE LISTING

```
<160> NUMBER OF SEQ ID NOS: 1

<210> SEQ ID NO 1
<211> LENGTH: 1459
<212> TYPE: DNA
<213> ORGANISM: Unknown
<220> FEATURE:
<223> OTHER INFORMATION: Paenibacillus elgii AM67

<400> SEQUENCE: 1
gacgaacgct ggcggcgtgc ctaatacatg caagtcgagc ggacccttcg gggttagcgg      60
cggacgggtg agtaacacgt aggcaacctg cctgtaagac tgggataact accggaaacg     120
gtagctaaga ccggataagt gattctytyg catgagagga tcaagaaaca cggggcaacc     180
tgtgacttac agatgggcct gcggcgcatt agctagttgg tggggtaacg gctcaccaag     240
gcgacgatgc gtagccgacc tgagagggtg atcggccaca ctgggactga gacacggccc     300
agactcctac gggaggcagc agtagggaat cttccgcaat ggacgcaagt ctgacggagc     360
aacgccgcgt gagtgatgaa ggttttcgga tcgtaaagct ctgttgccag ggaagaacgt     420
cgtggagagt aactgctctg cgaatgacgg tacctgagaa gaaagccccg gctaactacg     480
tgccagcagc cgcggtaata cgtaggggc aagcgttgtc cggaattatt gggcgtaaag     540
cgcgcgcagg cggccgctta agtctggtgt ttaagcccga ggctcaacct cggttcgcac     600
tggaaactgg gtggcttgag tgcaggagag gaaagcggaa ttccacgtgt agcggtgaaa     660
tgcgtagaga tgtggaggaa caccagtggc gaaggcggct ttctggcctg taactgacgc     720
tgaggcgcga aagcgtgggg agcaaacagg attagatacc ctggtagtcc acgccgtaaa     780
cgatgagtgc taggtgttag gggtttcgat acccttggtg ccgaagtaaa cacaataagc     840
actccgcctg gggagtacgc tcgcaagagt gaaactcaaa ggaattgacg gggacccgca     900
caagcagtgg agtatgtggt ttaattcgaa gcaacgcgaa gaaccttacc aggtcttgac     960
atccctctga atatcctaga gatagggtag gccttcggga cagaggagac aggtggtgca    1020
tggttgtcgt cagctcgtgt cgtgagatgt tgggttaagt cccgcaacga gcgcaaccct    1080
tgaacttagt tgccagcatt gagttgggca ctctaagttg actgccggtg acaaaccgga    1140
ggaaggtggg gatgacgtca aatcatcatg ccccttatga cctgggctac acacgtacta    1200
```

```
caatggccgg tacaacggga agcgaagtcg cgagatggag ccaatcctaa gaaagccggt    1260
ctcagttcgg attgcaggct gcaactcgcc tgcatgaagt cggaattgct agtaatcgcg    1320
gatcagcatg ccgcggtgaa tacgttcccg ggtcttgtac acaccgcccg tcacaccacg    1380
agagtttaca cacccgaag tcggtggggt aaccgcaagg agccagccgc cgaaggtggg     1440
gtagatgatt ggggtgaag                                                 1459
```

PAENIBACILLUS ELGII AM-67 STRAIN AND BIOPESTICIDE COMPOSITION CONTAINING SAME

CROSS-REFERENCE TO RELATED APPLICATIONS

This application is a continuation application, and claims the benefit under 35 U.S.C. § 120 and § 365 of PCT Application No. PCT/KR2018/001253, filed on Jan. 29, 2018, which is hereby incorporated by reference. PCT/KR2018/001253 also claimed priority to Korean Patent Application No. 10-2018-0007953 filed on Jan. 22, 2018 and Korean Patent Application No. 10-2018-0010792 filed on Jan. 29, 2018, both of which are hereby incorporated by reference.

SEQUENCE LISTING IN ELECTRONIC FORMAT

The present application is being filed along with an Electronic Sequence Listing as an ASCII text tile via EFS-Web. The Electronic Sequence Listing is provided as a file entitled NAM011002C1_SEQLIST.txt, created and last saved on Feb. 12, 2020, which is 2,492 bytes in size. The information in the Electronic Sequence Listing is incorporated herein by reference in its entirety.

BACKGROUND

Technical Field

The present disclosure relates to novel *Paenibacilius elgii* AM-67 strain having antibacterial activity on phytobacterial pathogens causing Chinese cabbage soft rot disease, and an environmentally friendly biopesticide containing the same.
Related Technology Chinese cabbage (*Brassica campestris* subsp. *napus* var *pekinensis*) is a biennial plant belonging to Cruciferae, which is used as the main ingredient of kimchi, and is one of the highly produced and consumed vegetables in Korea. Along with the well-being boom in recent years, kimchi has been recognized for its food and nutritional value, and thus is growing in demand not only in the Korean domestic market but also in the world market. Chinese cabbage is a cryophilic vegetable that likes the cool climate; and in a case where Chinese cabbage grows above 20° C. that is an optimum growth temperature, the Chinese cabbage is affected in terms of head formation and appearance of bacteria (*Erwinia carotovora* subsp. *carotovora*) causing a soft rot disease results in decreased production and deteriorated quality (Opena et al., 1988; De Boer and Kelman, 1978 *Potato Res.*; Stommel et al., 1996, *Plant Dis.*; Eun-Kyoung Chung, 2003 The Korean Journal of Pesticide Science; Hee-Young Kwon et al., 2009 Journal of Life Science; Anupama et al., 2009, The Korean Journal of Pesticide Science; Korean Patent No. 580336 owned by Chunghuk National University Industry Academy Cooperation Foundation). The Chinese cabbage soft rot disease is a plant infectious disease caused by *Erwinia carotovora* subsp. *carotovora*; and such a disease is a bacterial disease that causes damage to various vegetables, including Chinese cabbage, radish, potato, carrot, and the like. The Chinese cabbage soft rot disease is a bacterial soil disease that has a very low chemical controlling effect, and thus prophylactic application must be done. Various methods are used to control bacterial soft rot diseases. Among these, chemical controlling is mainly used due to the very high cost of soil fumigation. However, in a case where chemical pesticides are used, such chemical pesticides kill other useful soil microorganisms as well; and use of agricultural antibiotics results in emergence of resistant bacteria, thereby causing a variety of problems.

Biopesticides, which are environmentally friendly controlling agents, do not cause these problems, and have safety and little toxicity to human and livestock. In general, the biopesticides utilize microorganisms widely present in nature, and thus may minimize problems of ecosystem disturbance. Recently, development of environmentally friendly microbial pesticides has been spurred, and many attempts have been made. However, the result is merely a composition using a culture solution. Currently, regarding microorganisms for controlling soft rot diseases, the following subject matters have been reported: novel *Bacillus* sp. microorganism having effect of protection on Chinese cabbage bacterial soft-rot disease (Korean Patent No. 580336); novel *Streptomyces* sp. strain with quorum sensing inhibition activity (Korean Patent No. 1206883); Piericidin A1 with competitive inhibitory activity of acyl homoserine lactone (Korean Patent No. 743673); in a case where an enzyme (lactonase) that degrades homoserine lactone, a quorum sensing signal substance, in phytopathogenic bacteria, is isolated from microorganisms, and is transformed into potato and tobacco, resistance is induced against a soft rot disease caused by pathogenic bacteria in which pathogenic factors are induced by quorum sensing signals (Korean Patent Application No. 2003-7002587); and novel strains of *Lactobacillus* KLFOI and *Lactococcus* KLC02 and compositions for controlling plant disease using same (Korean Patent No. 1010537).

As described above, up to now, most studies have been conducted on inhibition of Chinese cabbage soft rot disease through control of quorum, and transformation of Chinese cabbage using *Bacillus, Lactobacillus*, and genetic modification.

SUMMARY OF CERTAIN INVENTIVE ASPECTS

One inventive aspect is to isolate a novel microbial strain that controls *Erwinia* sp. bacteria causing Chinese cabbage soft rot disease, and to provide a biopesticide containing the same.

Another aspect is a method including designating a strain, which is obtained through total genomic analysis and consists of a total chromosome length of 8,072,494 bp, as *Paenibacillus elgii* AM-67, and depositing the strain with Korea Research institute of Bioscience and Biotechnology on Jan. 23, 2018 under Accession No. KCTC 13466BP; and a step of identifying, with a culture composition obtained from culture using the isolated strain of the present disclosure and a crude extract thereof, its antibacterial activity on *Erwinia* bacteria causing Chinese cabbage soft rot disease, and evaluating its use as an environmentally friendly biological material.

Another aspect is a controlling method in which soil or plants are treated with controlling agents for Chinese cabbage soft rot disease and similar soft rot diseases through various formulation schemes using the strain and its culture solution or an extract thereof.

At least one of the disclosed embodiments provides an excellent effect from the viewpoint of providing novel Paenibacillus elgii AM-67 strain that controls Chinese cabbage soft rot disease, and a hiopesticide containing the same.

DETAILED DESCRIPTION OF CERTAIN INVENTIVE EMBODIMENTS

The present disclosure relates to biological control against Erwinia sp. causing a bacterial rot disease that is Chinese cabbage blight, using the isolated strain Paenibacillus elgii AM-67 (Accession No. KCTC 13466BP). The gene of the newly isolated strain of the present disclosure is related to a novel microbial Paenibacillus elgii AM-67 strain, having a chromosomal nucleotide sequence consisting of a total length of 8,042,494 bp, and a biopesticide containing the same controls soil microorganism-induced Chinese cabbage soft rot disease caused by infection through the roots during a growth period for Chinese cabbage cultivation, so that the Chinese cabbage soft rot disease is effectively controlled in a case where the biopesticide is applied on the Chinese cabbage field. Thus, a biopesticide containing a culture composition, which contains the Paenibacillus elgii AM-67 strain, and/or an extract thereof provides an environmentally friendly biopesticide material that enables environmentally friendly cultivation.

Some embodiments of the present disclosure provide Paenibacillus elgii ANI-67 (KCTC 13466BP), its culture composition, and a crude extract thereof, which control Chinese cabbage soft rot disease.

Other embodiments of the present disclosure provide a basis for control activity of a culture composition on Erwinia causing Chinese cabbage soft rot disease, the culture composition containing, as an active ingredient, the microorganism of the present disclosure, its culture solution, or a crude extract thereof.

Hereinafter, embodiments of the present disclosure will be described in detail by way of examples.

EXAMPLE 1

Isolation and Selection of Bacteria Showing Antibacterial Activity on Erwinia Causing Chinese Cabbage Soft Rot Disease To isolate microorganisms showing antibacterial activity on Erwinia causing Chinese cabbage soft rot disease, soil samples were suspended and diluted in sterile physiological saline, inoculated in LB agar medium, and cultured at 30° C. for 2 days, so that isolation of microorganisms was performed.

Among the purely isolated strains, to isolate and select strains having antibacterial activity on Chinese cabbage soft rot disease, culture supernatants of the respective strains were used to select strains showing antibacterial capacity.

Figure 1:
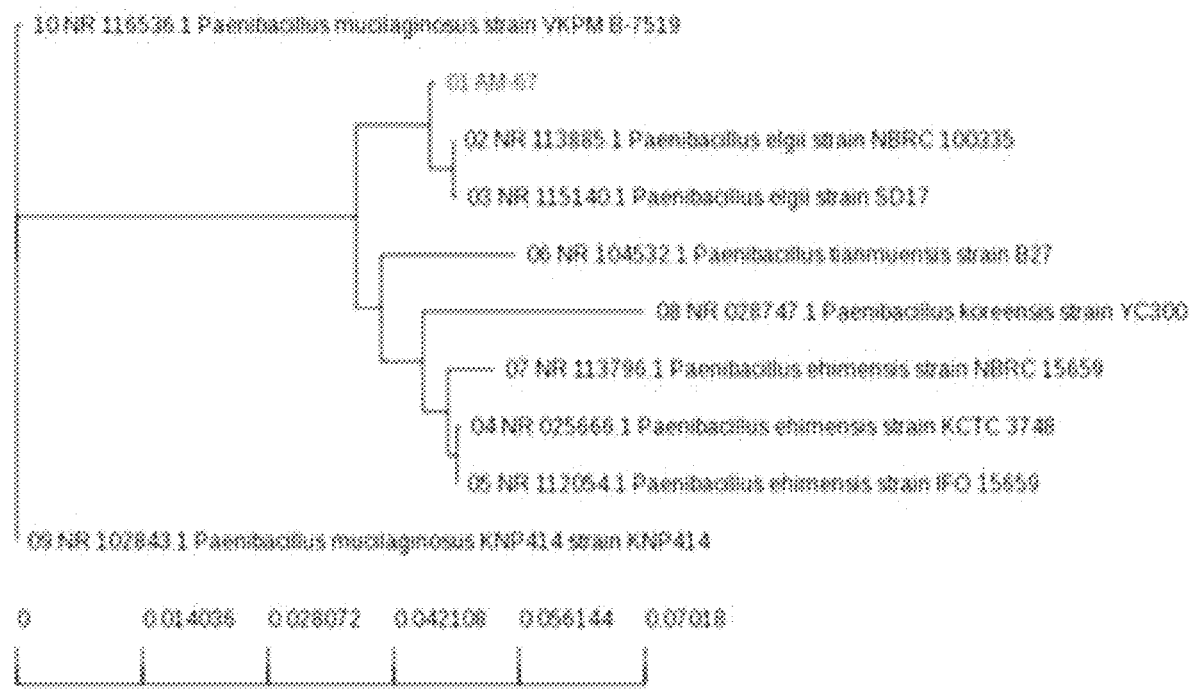
FIG. 1 illustrates a diagram showing taxonomic classification obtained by 16s rRNA sequencing for identification of the novel microbial strain of the present disclosure.

16S rRNA sequencing was performed for taxonomic identification of the bacteria having antibacterial activity, and the strain having excellent final antibacterial activity was deposited with Korea Research Institute of Bioscience and Biotechnology, designated as a depositary institution for microorganisms under the Budapest Treaty, on Jan. 23, 2018 under Accession No. KCTC 13466BP (FIG. 1)

EXAMPLE 2

Genetic Analysis of Antagonistic Bacteria of Present Disclosure

For genetic analysis of antagonistic bacteria of the present invention, such analysis was performed through whole genome de novo sequencing. A request for the analysis was made to Macrogen Inc. Consensus sequences as shown in Table 1 were obtained by the de novo assembly approach (see SEQ ID NO: 1).

TABLE 1

| Summary of assembly | | | | | |
|---|---|---|---|---|---|
| Contig Name | Total Length | N50 | Max Length | Min Length | Avg Length |
| contig 1 | 8,042,494 | 8,042,494 | 8,042,494 | 8,042,494 | 8,042,494 |

[Note]
Number of Contigs: The number of contigs assembled.
Total Length: The total length of contigs.
N50: 50% of all bases come from contigs longer than this value.
Max Length: The length of maximum contig.
Mm Length: The length of minimum contig.
Avg Length: The average length of contigs assembled.

EXAMPLE 3

Performing of Genome Annotation of Microbial Strain of Present Disclosure

Figure 2:
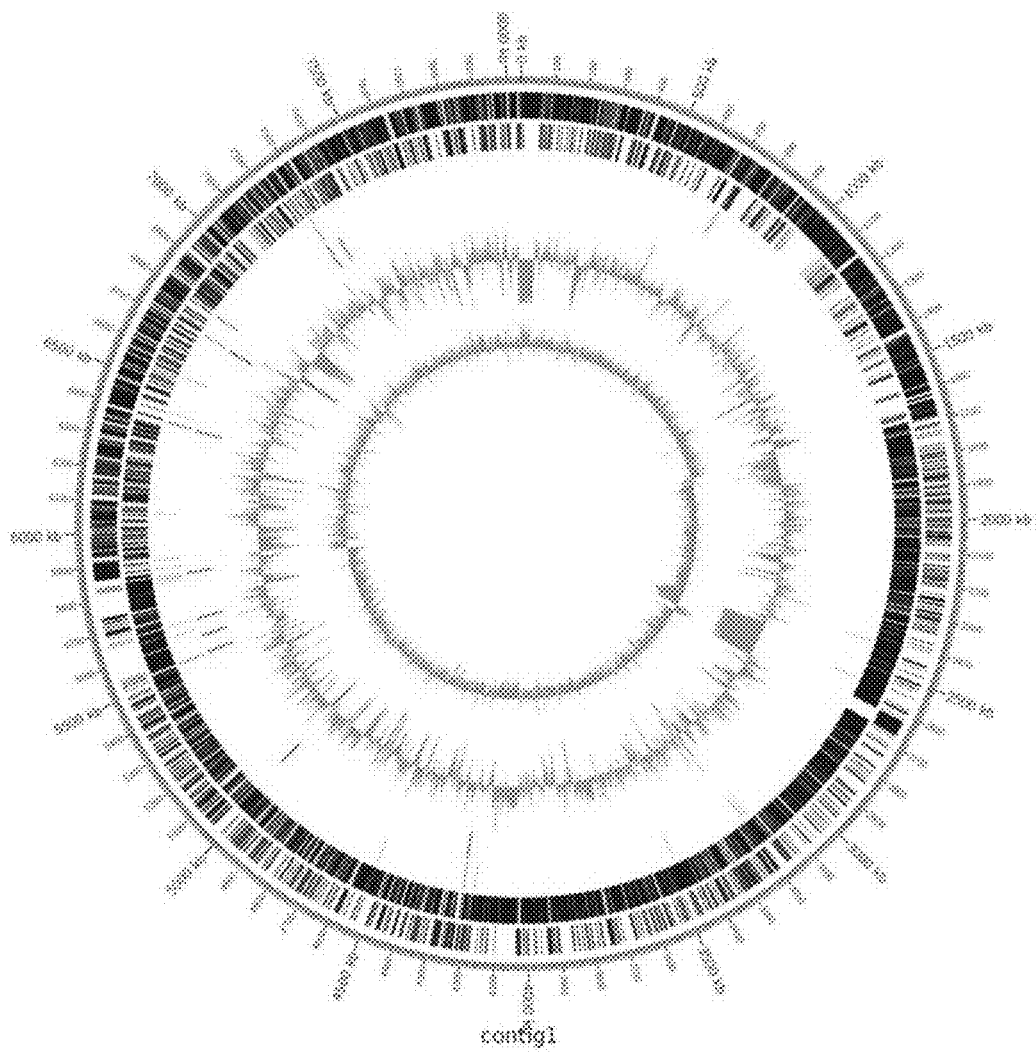
FIG. 2 illustrates a genetic map of the novel microbial strain of the present disclosure.

For genetic analysis of the antagonistic bacteria of the present disclosure, genome annotation, which had been completed through whole genome de novo sequencing, was performed. Table 2 shows CDS, tRNA, and rRNA which have been completed from sequencing based on genomic data analysis for the strain of the present disclosure, and the final completed genetic map is illustrated in FIG. 2.

TABLE 2

| 7,369 CDS, 96 tRNA, 30 rRNA genes were discovered in present disclosure | | | | |
|---|---|---|---|---|
| Contig Name | Length (bp) | CDS | tRNA | rRNA |
| contig 1 | 8,042,494 | 7,369 | 96 | 30 |
| Total | 8,042,494 | 7,369 | 96 | 30 |

[Note]
Length (bp): The number of bases in each contig
CDS: Coding Sequence
tRNA: Transfer RNA, tRNA has triplet nucleotide sequence complementary to the triplet nucleotide coding sequences of messenger RNA (mRNA)
rRNA: Ribosomal RNA, a molecular component of ribosome

EXAMPLE 4

Measurement of Culture Conditions for Microbial Strain of Present Disclosure and Antibacterial Activity Thereof Culture conditions that allow the antagonistic bacteria of the present disclosure to have control capacity on *Erwinia* causing Chinese cabbage soft rot disease, and antibacterial activity of the antagonistic bacteria were measured.

The microbial *Paenibacillus elgii* AM-67 strain of the present disclosure was cultured at 30° C. for 3 days in a medium supplemented with 3% glucose, 3% yeast extract, and 5% NaCl. Then, the culture supernatant was taken, and antibacterial control activity thereof was identified using the disk diffusion method generally known for *Erwinia* causing Chinese cabbage soft rot disease. 100 μL of the culture supernatant of *Paenibacillus elgii* AM-67 strain of the present disclosure was loaded on each test disk and drying was performed. Then, the disk was placed on a medium smeared with *Erwinia* causing Chinese cabbage soft rot disease, and examined for antibacterial activity level thereof.

Figure 3:
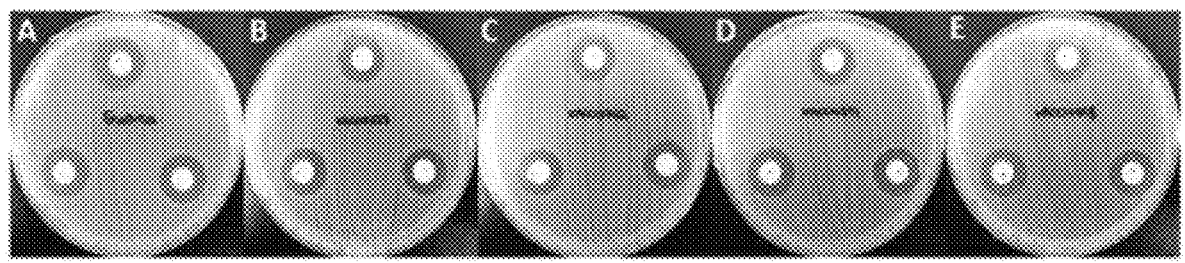
FIG. 3 illustrates pictures showing antibacterial activity of the novel microbial strain of the present disclosure on Chinese cabbage soft rot disease.

As a result of the experiments, it was examined that the strain shows antibacterial activity on *Erwinia* causing Chinese cabbage soft rot disease (FIG. 3).

EXAMPLE 5

Figure 4:
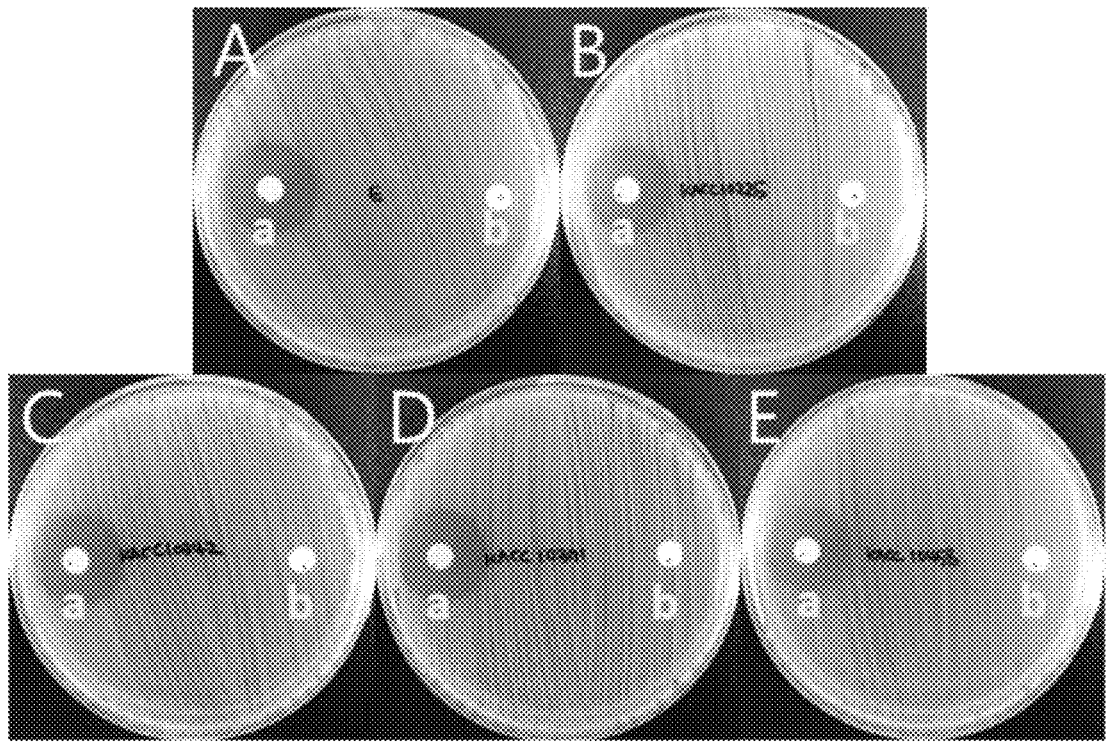
FIG. 4 illustrates pictures showing antibacterial control activity of microbial strain of the present disclosure using the disk diffusion method.

Control Activity for Inhibition of Soft Rot Disease in Case of Using Solvent Extract of Culture Supernatant of *Bacillus* sp. AM-67 Strain of Present Disclosure Experiments were carried out to identify inhibition capacity, on Chinese cabbage soft rot disease, of an organic solvent crude extract of the culture supernatant of the antagonistic bacterial *Paenibacillus elgii* AM-67 strain of the present disclosure. The culture supernatant was extracted stepwise with hexane, chloroform, ethyl acetate, and butanol, to obtain a crude extract, and antibacterial control activity thereof was identified by using the disk diffusion method generally known for *Erwinia* causing Chinese cabbage soft rot disease. The experimental results are illustrated in FIG. 4.

---

What is claimed is:

1. A biopesticide composition for Chinese cabbage soft rot disease caused by *Erwinia* sp., comprising, as an active ingredient, an extract including:
   chloroform;
   a supernatant of a culture solution comprising *Paenibacillus elgii* AM-67 strain (KCTC 13466BP), 3% glucose, 3% yeast extract, and 5% NaCl.

2. The biopesticide composition of claim 1, wherein the *Paenibacillus elgii* AM-67 strain comprises a nucleotide sequence of SEQ ID NO: 1.

* * * * *

UNITED STATES PATENT AND TRADEMARK OFFICE
CERTIFICATE OF CORRECTION

PATENT NO. : 11,800,871 B2
APPLICATION NO. : 16/789942
DATED : October 31, 2023
INVENTOR(S) : Gi Seok Kwon It is certified that error appears in the above-identified patent and that said Letters Patent is hereby corrected as shown below:

On the Title Page

Column 1 Item (56) (Foreign Patent Documents), Line 1, delete "KP" and insert -- KR --.

Column 2 Item (56) (Other Publications), Line 28, delete "Shanshua," and insert -- Shanhua, --.

In the Specification

Column 1, Line 22 (approx.), delete "tile" and insert -- file --.

Column 1, Line 33, delete "Paenibacilius" and insert -- Paenibacillus --.

Column 1, Line 38, delete "var" and insert -- *var.* --.

Column 1, Line 57, delete "Chunghuk" and insert -- Chungbuk --.

Column 2, Line 33 (approx.), delete "KLFOI" and insert -- KLF01 --.

Column 2, Line 53, delete "institute" and insert -- Institute --.

Column 3, Line 2, delete "hiopesticide" and insert -- biopesticide --.

Column 3, Line 15 (approx.), line After "activity of" insert -- the novel --.

Column 3, Line 40, delete "ANI-67" and insert -- AM-67 --.

Column 4, Line 7, delete "(FIG. 1)" and insert -- (FIG. 1). --.

Column 4, Line 35, delete "Mm" and insert -- Min --.

Signed and Sealed this
Thirtieth Day of January, 2024

Katherine Kelly Vidal
*Director of the United States Patent and Trademark Office*